United States Patent [19]

Drewlow

[11] Patent Number: Plant 6,635

[45] Date of Patent: Feb. 28, 1989

[54] STREPTOCARPUS PLANT NAMED ACHILLES

[75] Inventor: Lyndon W. Drewlow, Ashtabula, Ohio

[73] Assignee: Mikkelsens, Inc., Ashtabula, Ohio

[21] Appl. No.: 42,104

[22] Filed: Apr. 22, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Streptocarpus plant named Achilles, characterized by its distinct dark red flower color, semi-compact growth habit, ease of propagation, highly floriferous and continuous flowering habits, and by its ability to flower both under low light and high temperature conditions.

1 Drawing Sheet

The present invention relates to a new and distinctive cultivar of Streptocarpus plant, botanically known as *Streptocarpus*×*hybridus*, and referred to by the cultivar name Achilles. The new cultivar was developed by me through controlled breeding by crossing Mikkelsen Seedling 82-1160-1 (seed parent)×Mikkelsen Seedling 82-1272-3 (pollen parent).

Asexual reproduction by leaf cuttings at Ashtabula has shown that the unique features of Achilles are stabilized and are reproduced true to type in successive propagations.

The following characteristics distinguish Achilles from both its parent varieties and other cultivated Streptocarpus of this type known and used in the floriculture industry. In the characteristic comparisons, the cultivars Electra, Ulysses, Ariadne, and Muse are disclosed in pending applications.

1. Achilles has a distinct dark red flower, with Apollo having reddish pink flowers and only having dark red streaking extending from throat to lower 3 petals. Electra is a carmine color and Ulysses is a violet purple.

2. Flower size of Achilles is similar to Apollo, Ulysses and Ariadne, and larger than Muse and Electra. Overlap of lobes of petals is less than Ulysses and similar to Apollo, with Muse, Electra and Ariadne having no overlap of lobes.

3. Achilles has a purple calyx in the bud stage and turning green when flowers open, which is similar to Electra. Ulysses remains with a heavy purple cast on mature flowers. Muse, Apollo, and Ariadne have a green calyx both on the bud and open flower.

4. The filament on Achilles has a dark red area about two-thirds of the way up to the anther, while Ulysses has a purple area in the same location; Ariadne is entirely white with a pinkish cast; Apollo is white with reddish cast; Muse is white, and Electra is carmine on the upper one-third of filament.

5. Achilles has a purple ovary with white style which is similar to Electra, Ariadne and Muse; Apollo has a green ovary with purple cast and a white style, while Ulysses has a green with purple cast ovary and white style with purple hairs.

6. Achilles is similar to Ulysses in plant height and spread, and similar in height to Apollo but less spread. Ariadne is slightly more compact, and Muse and Electra are still more compact.

7. Achilles is very floriferous due to the large number of flower stalks produced per leaf axil and the average per flower stalk. It is similar in flowering habit to Ulysses and Apollo, but has more blooms per flower stalk than Apollo. Ariadne, Muse and Electra have more compact flower stalks.

8. leaves of Achilles are smaller than Apollo, similar to Ulysses. Ariadne, Muse and Electra all have narrower, slightly shorter leaves.

9. Achilles propagates very well from a leaf cutting, producing numerous plantlets in 8 to 10 weeks, depending on the time of year. From a well rooted plant from a 72 cell pack, a well developed flowering plant is obtained in 6 to 10 weeks in a 10 cm pot.

10. Achilles has shown the ability to flower both under the lower light conditions of winter (December to February) and under high temperatures of summer (July to September) without going out of bloom under greenhouse conditions.

The accompanying color photographs illustrate the overall appearance of Achilles. The photograph at the top is a perspective view of a plant of Achilles, with the flower color being a much lighter red than the actual flower color. The photograph at the bottom is a black and white photo which has been colored to show the flower color as accurately as possible.

The following is a detailed description of my new Streptocarpus cultivar based on plants produced under commercial practices in the greenhouses of Mikkelsens Inc., Ashtabula, Ohio 44004. Color references are made to The Royal Horticultural Society Colour Chart (R.H.S.), except where general colors of ordinary dictionary significance are used.

Parentage: Controlled cross between Mikkelsen seedling 82-1160-1 and Mikkelsen seedling 82-1272-3.

Propagation:

A. *Type cutting.*—Leaf.

B. *Time to develop plantlets.*—Summer: 8 weeks at 20° C.; Winter: 10 weeks at 20° C.

C. *Rooting habit.*—Numerous, fine, fibrous.

Plant description:

A. *Form.*—Leaves rosette from a crown at the soil line with flower stalks forming at the leaf midrib. Many leaves in a symmetrical pattern.

B. *Habit of growth.*—Flowers freely, never going out of bloom once it starts blooming under greenhouse conditions. Semi-compact, vigorous, spreading, flowers carried above foliage.

C. *Height from soil line.*—20 to 22 cm at maturity in 10 cm pot.

D. *Spread.*—50 to 55 cm at maturity. Leaf Size: 20 to 25 cm long and 8 to 10 cm wide at the widest point; leaf size can vary greatly with cultural conditions. Quantity: Mature plant can have more than 20 leaves. Leaf Shape: Elliptical. Texture: Lower surface rugose with veins protruding and pubescent; upper surface rugose and pubescent. Margin: Finely crenate. Color: Young foliage top side 147B; under side 147C. Mature foliage top side 147B; under side 146D. Ribs and veins: Pinnate. Rib and vein color: 146B. Leaf tips: Obtuse. Leaf base: Acute.

Flowering description: Flowers open one at a time on the individual flower stalks.

A. *Fully expanded.*—50 to 55 mm.

B. *Stem.*—Single, reddish green in color, long, slightly pubescent and round — several from a leaf midrib.

C. *Form.*—Funnel shaped with upper two petals reflexed and smaller; lower petals flattened and larger to give an overall flat appearance.

D. *Flower bud description.*—25 to 28 mm long at maturity, tubular with the end larger in diameter than the rest, 5 reddish-green calyx folded over basal end.

E. *Flowers borne.*—In clusters of 3 to 7 flowers per flower stalk, with 6 the most common. Flowers are carried above foliage. Pedicels of the flowers in the inflorescence vary in length. Terminal flower opens first.

F. *Quantity of flowers.*—Mature plant can have more than 15 flower stalks open, with up to 4 open at one time on each.

G. *Permanence.*—Long lasting, 10 days or longer.

Color:

A. *Tonality from a distance.*—Dark red.

B. *Upper surface of petals.*—Between 53A and 53B.

C. *Reverse of petals.*—186B.

D. *Throat.*—53A with lighter streaking especially in the upper two petals.

E. *Discoloration.*—Fades to a lighter red as petals age, especially under high temperature and light.

Petals:

A. *Texture.*—Satin.

B. *Appearance.*—Individually lobed with slight crenate margins; top 2 petals are reflexed and smaller, overlap. Bottom 3 are flat and overlap slightly. No overlap between the 2 upper and 3 lower petals.

C. *Arrangement.*—Regularly united into an almost circular shape.

D. *Persistence.*—10 days or longer; petals remain on plant in dry form until picked.

E. *Fragrance.*—None.

Reproductive organs:

A. *Stamens.*—2 fertile, 2 sterile; small. Anther shape: 2 fertile; interconnected and flat. Anther color: White with red cast. Filament: White about ⅔ of the way to anther, then a 2 mm red area followed by white to anther. Pollen color: Cream.

B. *Pistils.*—Stigma shape: 2 lobed flattened, rounded at end of lobes. Stigma color: White with red cast. Stigma size: 2 mm. Style color: White. Style size: 8–9 mm. Ovaries: Numerous, 16–18 mm on a receptive pistil, green with purple cast.

Disease resistance: No disease problems observed to date.

OTHER IMPORTANT CHARACTERISTICS

1. Semi-compact growth habit with relatively small pliable leaves make Achilles ideal for shipping and 10 cm pot plant production.

2. Leaves do not spot when watered with cold (40°) water.

3. Leaves do not bronze when exposed to moderate levels of light.

I claim:

1. A new and distinct Streptocarpus plant named Achilles, as illustrated and described, and particularly characterized by its distinct dark red flower color, semi-compact growth habit, ease of propagation, highly floriferous and continuous flowering habits, and its ability to flower both under low light and high temperature conditions.

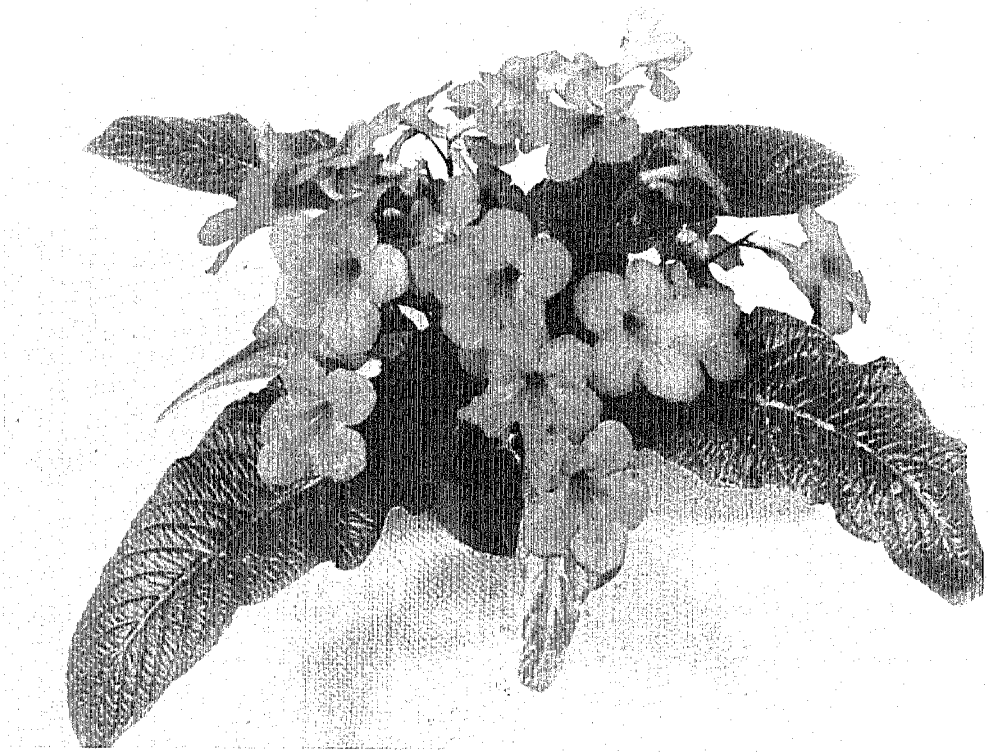
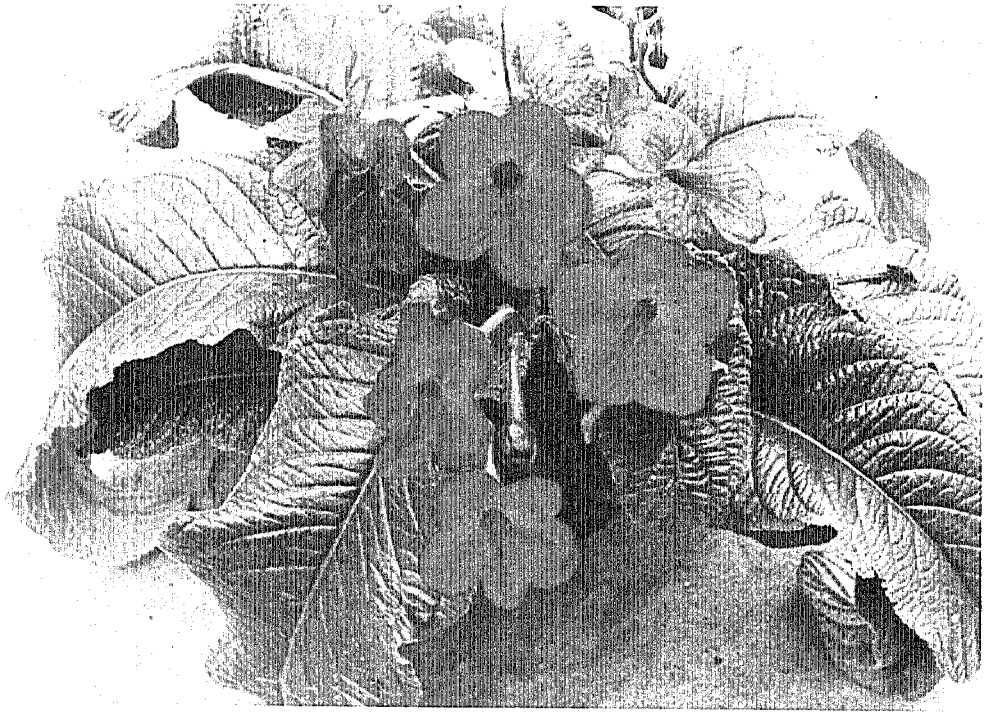

* * * * *